US012053333B2

(12) United States Patent
El Amm

(10) Patent No.: US 12,053,333 B2
(45) Date of Patent: Aug. 6, 2024

(54) SURGICAL ENHANCED VISUALIZATION SYSTEM AND METHOD OF USE

(71) Applicant: The Board of Regents of the University of Oklahoma, Norman, OK (US)

(72) Inventor: Christian El Amm, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 435 days.

(21) Appl. No.: 16/840,254

(22) Filed: Apr. 3, 2020

(65) Prior Publication Data

US 2020/0315734 A1    Oct. 8, 2020

Related U.S. Application Data

(60) Provisional application No. 62/829,559, filed on Apr. 4, 2019.

(51) Int. Cl.
*G06T 19/00* (2011.01)
*A61B 34/10* (2016.01)
(Continued)

(52) U.S. Cl.
CPC .............. *A61B 90/36* (2016.02); *A61B 34/10* (2016.02); *A61B 34/20* (2016.02); *G02B 27/017* (2013.01);
(Continued)

(58) Field of Classification Search
CPC ......... A61B 90/36; A61B 34/10; A61B 34/20; A61B 2034/105; A61B 90/30;
(Continued)

(56) References Cited

U.S. PATENT DOCUMENTS 9,892,564 B1    2/2018  Cvetko et al.
10,010,379 B1   7/2018  Gibby et al.
(Continued)

OTHER PUBLICATIONS

Unknown author, https://www.f35.com/about/capabilities/helmet.
(Continued)

*Primary Examiner* — Grace Q Li
(74) *Attorney, Agent, or Firm* — Crowe & Dunlevy, P.C.

(57) ABSTRACT

A method for using a surgical enhanced visualization system for enhancing a surgical operation includes the steps of acquiring patient reference data, loading the patient reference data and features into the computer, and acquiring live data from the operating suite during the surgical operation, where the live data includes a live three dimensional model of the patient. The method continues with the steps of registering the patient reference data and live data and displaying in real time an overlay of selected registered patient reference data onto the patient through the headset worn by the surgeon. The surgical enhanced visualization system may include a computer adapted to store reference data, a sensor module inside the surgical suite that is configured to record live data during the surgical procedure, and an augmented reality headset configured to display both live data and reference data to the surgeon during the surgical procedure.

16 Claims, 6 Drawing Sheets

(51) Int. Cl.
| | |
|---|---|
| *A61B 34/20* | (2016.01) |
| *A61B 90/00* | (2016.01) |
| *G02B 27/01* | (2006.01) |
| *G06N 20/00* | (2019.01) |
| *G06T 7/38* | (2017.01) |
| *G06T 19/20* | (2011.01) |

(52) U.S. Cl.
CPC ............... *G06N 20/00* (2019.01); *G06T 7/38* (2017.01); *G06T 19/006* (2013.01); *G06T 19/20* (2013.01); *A61B 2034/102* (2016.02); *A61B 2034/2046* (2016.02); *A61B 2090/365* (2016.02); *A61B 2562/02* (2013.01); *G06T 2210/41* (2013.01)

(58) Field of Classification Search
CPC ...... A61B 2034/2057; A61B 2090/371; A61B 2090/372; A61B 2090/502; G02B 27/017; G06N 20/00; G06T 7/38; G06T 19/006; G06T 19/20; G06T 2210/41; G06T 2207/10028; G06T 2207/10081; G06T 2207/30016; G06T 7/33
See application file for complete search history.

(56) References Cited

U.S. PATENT DOCUMENTS

| | | | |
|---|---|---|---|
| 10,159,530 | B2 | 12/2018 | Lang |
| 10,265,138 | B2 | 4/2019 | Choudhry et al. |
| 10,945,807 | B2 | 3/2021 | Gibby et al. |
| 10,952,809 | B2 | 3/2021 | Choudhry et al. |
| 10,964,291 | B2 | 3/2021 | Southworth et al. |
| 11,004,271 | B2 | 5/2021 | Cvetko et al. |
| 11,013,560 | B2 | 5/2021 | Lang |
| 11,138,806 | B1 | 10/2021 | Qian et al. |
| 11,172,996 | B1 | 11/2021 | Qian et al. |
| 11,237,627 | B2 | 2/2022 | Gibby et al. |
| 11,307,653 | B1 | 4/2022 | Qian et al. |
| 11,395,715 | B2 | 7/2022 | Choudhry et al. |
| 11,452,477 | B2 | 9/2022 | Blume et al. |
| 11,457,982 | B2 | 10/2022 | Marti et al. |
| 11,701,183 | B2 | 7/2023 | Martin et al. |
| 2009/0250621 | A1* | 10/2009 | Ohta .................... G03B 42/04 |
| | | | 235/382 |
| 2018/0293802 | A1 | 10/2018 | Hendricks et al. |
| 2018/0325618 | A1 | 11/2018 | Justin et al. |
| 2019/0011703 | A1* | 1/2019 | Robaina ................ A61B 34/25 |
| 2019/0049968 | A1* | 2/2019 | Dean ...................... A61G 5/04 |
| 2019/0350657 | A1* | 11/2019 | Tolkowsky ............. G06T 15/06 |
| 2020/0004351 | A1* | 1/2020 | Marchant ................ G06N 20/00 |
| 2020/0186786 | A1 | 6/2020 | Gibby et al. |
| 2021/0192759 | A1* | 6/2021 | Lang ..................... A61B 34/25 |
| 2022/0155854 | A1 | 5/2022 | Gibby et al. |

OTHER PUBLICATIONS

Fida B, Cutolo F, di Franco G, Ferrari M, Ferrari V. Augmented reality in open surgery. Updates Surg. Jul. 13, 2018. doi: 10.1007/s13304-018-0567-8. PubMed PMID: 30006832.

Amm CA, Denny AD. Correction of sagittal synostosis using foreshortening and lateral expansion of the cranium activated by gravity: surgical technique and postoperative evolution. Plast Reconstr Surg. Sep. 2005; 116(3):723-35. PubMed PMID: 16141807.

Beainy F, El Amm C, Abousleimane Y, Mapstone T, Beidas O, Workman M. Biomechanical effects of cranioplasty for defects using autogenous calvarial bone. J Craniofac Surg. Mar. 2012;23(2):e152-5. doi: 10.1097/SCS.0b013e31824cdc0d. PubMed PMID: 22446454.

El-Amm C, Le L, Dwyer J, Sawan K., Application of game-based 3D scanning in craniofacial analysis, Plast Reconstr Surg 133:226 Mar. 2014 DOI: 10.1097/01.prs.0000445049.54827.21.

Van Eijk RP, van der Zwan A, Bleys RL, Regli L, Esposito G. Novel Application of Postmortem CT Angiography for Evaluation of the Intracranial Vascular Anatomy in Cadaver Heads. AJR Am J Roentgenol. Dec. 2015;205(6): 1276-80. doi: 10.2214/AJR. 15.14500. PubMed PMID: 26587934.

Novarad Healthcare Enterprise Imaging; OpenSight Augmented Reality Surgery; 2020.

Medtronic; StealthStation System website; 2020.

* cited by examiner

SURGICAL ENHANCED VISUALIZATION SYSTEM AND METHOD OF USE

RELATED APPLICATIONS

This application claims the benefit of U.S. Provisional Patent Application Ser. No. 62/829,559 filed Apr. 4, 2019, entitled "Surgical Enhanced Visualization System and Method of Use," the disclosure of which is herein incorporated by reference.

BACKGROUND

Recent developments in virtual reality (VR) and augmented reality (AR) technologies have increased interest in the deployment of these technologies in the surgical theater. A number of companies are developing solutions that rely on the use by surgeons of AR and VR headsets. In some cases, an AR headset is worn by a surgeon during a procedure and supplemental information is displayed to the surgeon through the headset.

For example, U.S. Pat. No. 9,892,564 issued to Novarad Corporation discloses a system and method that includes the steps of identifying three-dimensional (3D) data for the patient (including external and internal layers), determining real-time morphometric measurements of the actual outer layer of the patient, automatically registering the position of the outer layer of 3D data with the real-time position of the outer layer of the patient, and displaying in the AR headset one of the inner layers from the 3D data onto real-time views of the outer layer of the patient. Thus, the use of AR headsets allows a surgeon to visualize the internal anatomy of a patient in a live, real-time environment.

Although a number of commercial systems are being introduced to the marketplace, the existing technologies can best be described as passive surgical navigation systems that are intended to be relied upon to aid the surgeon in planning operations. These systems are not, however, intended to more actively assist the surgeon during the operation. The present disclosure is directed to addressing these and other deficiencies in the prior art and provide a suite of surgical technologies that more actively assist the surgeon in the operating theater.

DETAILED DESCRIPTION

The present disclosure is directed, in non-limiting embodiments, to a surgical enhancement visualization system and associated technologies combining augmented reality displays and machine learning for improving the safety and efficacy of a surgical procedure. The system uses three-dimensional (3D) sensors and cameras to build a virtual model of the operating theater and surgical field. Preoperative imaging data is labeled (e.g. vessels, tumor, ventricle, bone, skin, etc.) and "registered" automatically (aligned in 6 degrees of freedom with the subject's external anatomy). Real time tracking of selected features of the operative field is done with various neural net architectures (for RGB and volumetric feeds) and allow real-time tracking of patient movement during surgery, surgeon's hands and finger position, and selected surgical instruments (e.g., a cautery pen). Various automatic (e.g., proximity) or manually activated (e.g., voice command) triggers result in an overlay display to the surgeon's field of view of information, warnings or highlighted anatomy. For example, using voice commands the surgeon may choose to visualize a CT scan slice at the location of the tip of the cautery.

Figure 1:
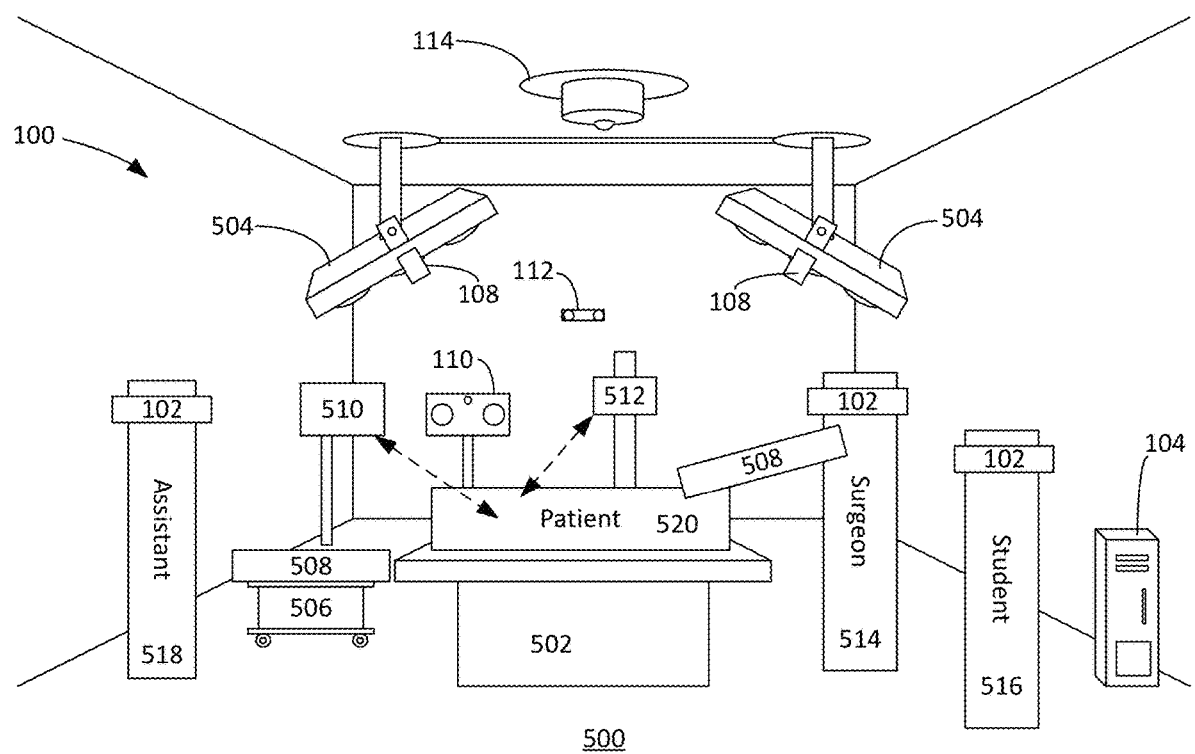
FIG. 1 depicts an operating suite in which an embodiment of the present invention has been deployed.
Figure 2:
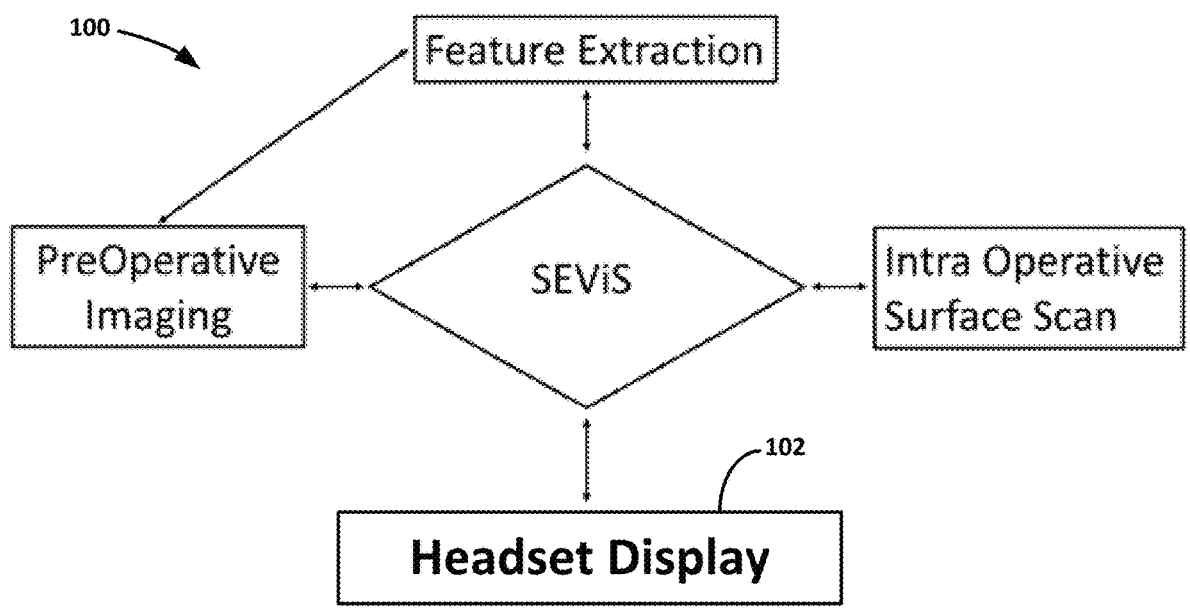
FIG. 2 is a flowchart that provides an overview the interaction between the surgical enhanced visualization system and external inputs and outputs.

Beginning with FIG. 1, shown therein is an embodiment of a surgical enhanced visualization system (SEViS) 100 deployed in an operating suite 500. As depicted, the operating suite 500 includes a surgical table 502, one or more overhead lights 504, an instrument cart 506, one or more instruments 508, a vital sign monitor 510, and an IV pole 512. A surgeon 514, a student 516, a surgical assistant 518 and a patient 520 are present in the operating suite 500. It will be appreciated that the depiction of the operating suite 500 in FIG. 1 is simply an example and that the operating suite 500 may include additional components, such as radiology equipment, life support systems and sanitization facilities. The surgical assistant 518 may include a nurse, anesthesiologist, instrument specialist, or other caregiver in the operating suite 500.

The SEViS 100 generally includes one or more headsets 102 that receive data from one or more computers 104. The headsets 102 are configured to be worn by the surgeon 514, student 516, assistant 518 and others observing the procedure from inside the operating suite 500 or outside the operating suite 500. The headsets 102 receive data from the one or more computers 104 through wired or wireless connections. Although a single computer 104 is depicted, it will be appreciated that the computer 104 may include a series of networked or distributed computers that are located outside the operating suite 500. The computers 104 are generally configured to receive data from a variety of sources, process the data and provide the processed data to the headsets 102 and other displays located within the operating suite 500. The computers can be configured, for example, to receive Live Data from the surgical theater 500 from the surgical table 502, instrument cart 506, instruments 508, vital sign monitor 510, IV pole 512 and other accoutrement within the surgical theater 500.

As used herein, the term "Live Data" refers to data provided in real time (or near real time) to the SEViS 100 from the surgical suite 500 or from other external sources. Live Data includes, for example, image data taken by the SEViS 100 in the surgical suite 500. By contrast, the term "Reference Data" refers to data generated outside of the real-time surgical environment. Reference Data includes, for example, preoperative imaging data, preexisting anatomical and morphological data, surgical process information, pharmaceutical information, information about surgical equipment and instruments, and surgeon procedural preferences. "Features" refers to specific elements extracted from the Reference Data that can be stored, selected and displayed using the SEViS 100. Features include, for example, vascular structures, internal organs, and desired objectives from plastic surgery.

The headsets 102 are configured to provide an augmented reality (AR) or virtual reality (VR) experience to the surgeon 514 and others wearing the headsets 102. In some embodiments, the headsets 102 are augmented reality headsets available from Microsoft Corporation under the "HoloLens" trademark. In exemplary embodiments, the headsets 102 are configured to provide a virtual image overlay to physical objects, including the patient 520, inside the operating suite 500.

In some embodiments, the SEViS 100 further includes one or more sensor modules 106 that obtain information in real time from the operating suite 500. The sensor modules 106 may include overhead sensors 108 mounted on the overhead lights 504, a mobile sensor module 110 and a wall-mounted sensor module 112. The overhead sensor modules 108 are positioned to match the directional focus of the overhead lights 504. The mobile sensor module 110 may be mounted to a mobile sensor stand (as depicted), positioned on a surgical instrument 508, or worn by the surgeon 514 or another person in the operating suite 500. In some embodiments, the headsets 102 include additional sensors modules 106. Each of the sensor modules 106 may include RGB cameras, depth sensors, audio microphones, radiation detectors, proximity sensors, infrared projectors and receivers, LIDAR systems, time-of-flight camera systems and other sensors. In exemplary embodiments, the sensor modules 106 each include stereoscopic or depth cameras that generate a real-time, three-dimensional digital images within the operating suite 500.

It will be appreciated that the sensor modules 106 may include different sensors and that in some embodiments fewer than all of the sensors modules 106 will be deployed. For example, in some embodiments, the overhead sensor modules 108 include a package of RGB cameras, depth sensors and microphones, while the mobile sensor module 110 includes an infrared projector and a monochrome CMOS sensor. In each case, the sensor modules 106 are configured to provide Live Data from the surgery suite 500 to the computer 104.

Turning to FIGS. 2-6, shown therein are various process flowcharts for a variety of different mechanisms for importing, processing and using Live Data and Reference Data with the SEViS 100. As noted in FIG. 2, the SEViS 100 is configured to acquire Reference Data, such as preoperative imaging data, from the computer 104 and to extract Features from the preoperative imaging Reference Data. The SEViS 100 is further configured to perform an intraoperative surface scan of the patient 520 and the equipment in the operating suite 500 and to correlate this Live Data with the preloaded Reference Data. The Live Data and Reference Data can be coordinated, registered (positional alignment), and provided to the headsets 102 in real time.

Figure 3:
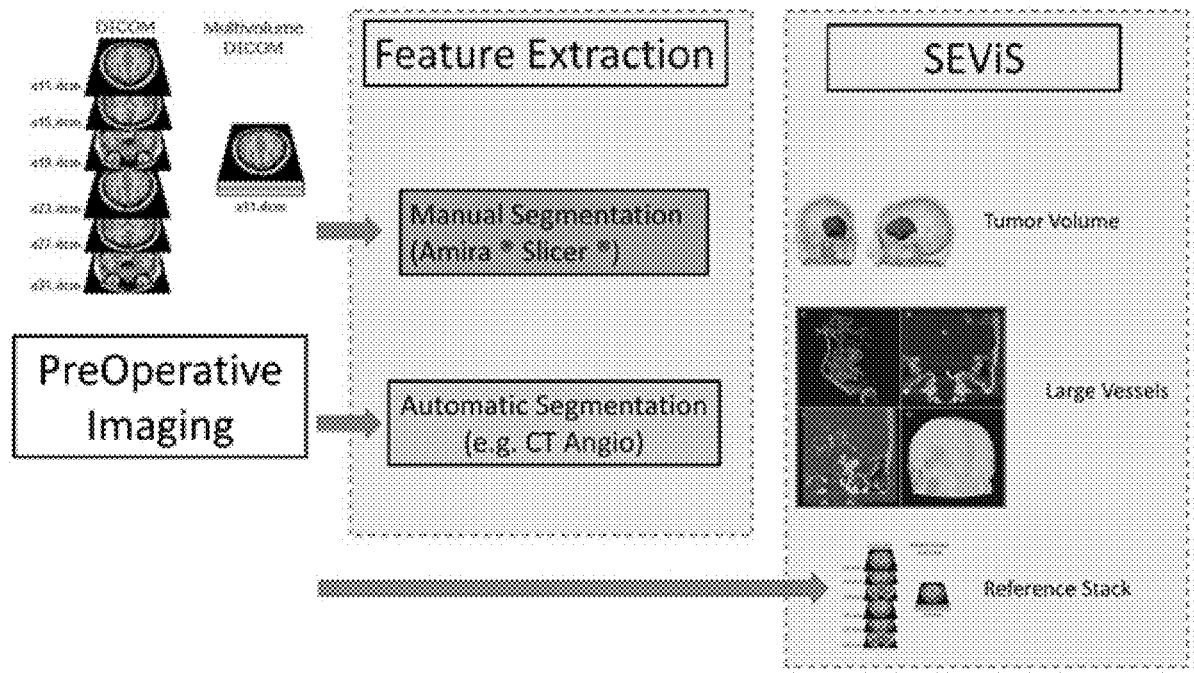
FIG. 3 is a graphical depiction of an example of the acquisition, processing and use of preoperative imaging data within the surgical enhanced visualization system.
Figure 4:
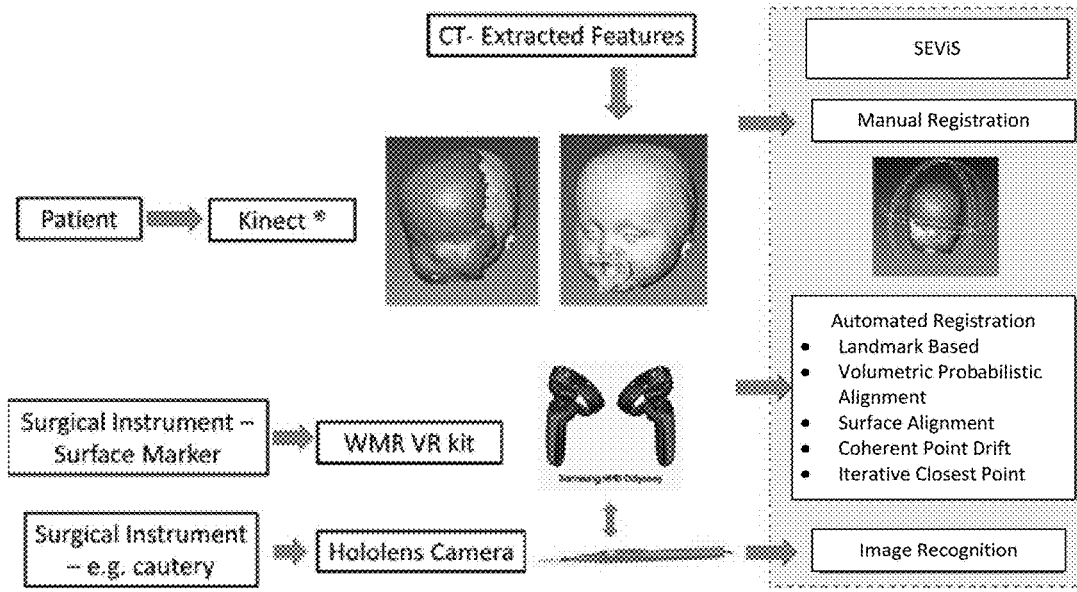
FIG. 4 is a graphical depiction of an example of the acquisition, processing and use of preoperative imaging data within the surgical enhanced visualization system.
Figure 5:
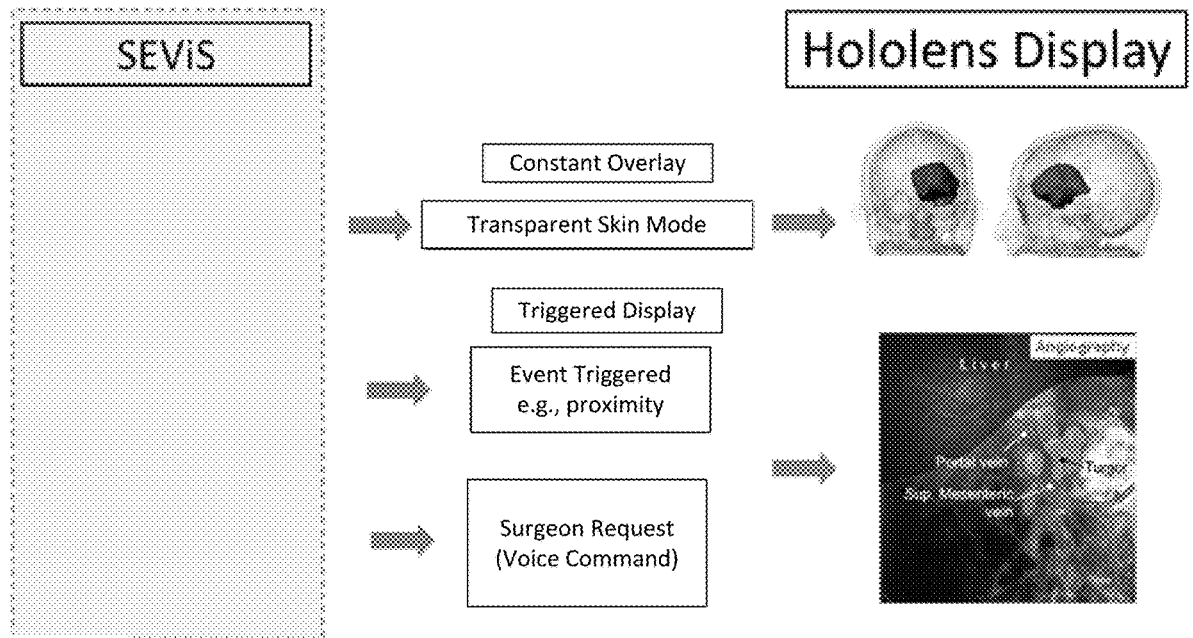
FIG. 5 is a graphical depiction of an example of the acquisition, processing and use of preoperative imaging data within the surgical enhanced visualization system.
Figure 6:
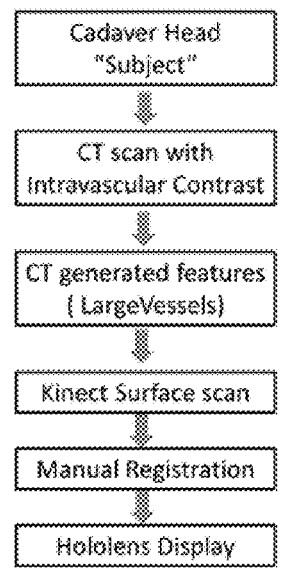
FIG. 6 is a process flowchart showing use of the surgical enhanced visualization system in a training exercise using a cadaver head.

Similarly, FIGS. 3 and 4 depict examples of loading preoperative imaging Reference Data obtained from radiological studies (e.g., computerized tomography (CT) scans and magnetic resonance imaging (MRI) scans). The SEViS 100 is configured to extract desired features from the preoperative imaging using manual and automatic segmentation techniques. The SEViS 100 is also configured to identify and track surgical instrument Live Data and to align and register the imaging Reference Data and instrument Live Data with the patient 520 and superimpose the Live Data and Reference Data onto the patient 520 in real time. As the relative positions of the surgeon 514 and patient 520 change in the operating suite 500, the SEViS 100 automatically updates the alignment and registration of the Live Data and Reference Data so that selected visual features can be displayed through the headset 102 in the appropriate position on the patient 520.

For example, as depicted and described in FIGS. 3-6, during the surgical operation, the surgeon 514 can select from a database of internal features extracted from the Reference Data and display those features within the headset 102 as if the surgeon was looking inside the patient 520. This enables the surgeon 514 to visualize internal features extracted from Reference Data, such as vascular structures and internal organs, while simultaneously tracking the position and encroachment of surgical instruments 508 relative to these features. A variety of methods for aligning, scaling and registering virtual images with a patient are disclosed in U.S. Pat. No. 10,010,379 issued to Gibby et al. and U.S. Pat. No. 9,892,564 issued to Cvetko et al., the entire disclosures of which are hereby incorporated herein by reference.

Figure 7:
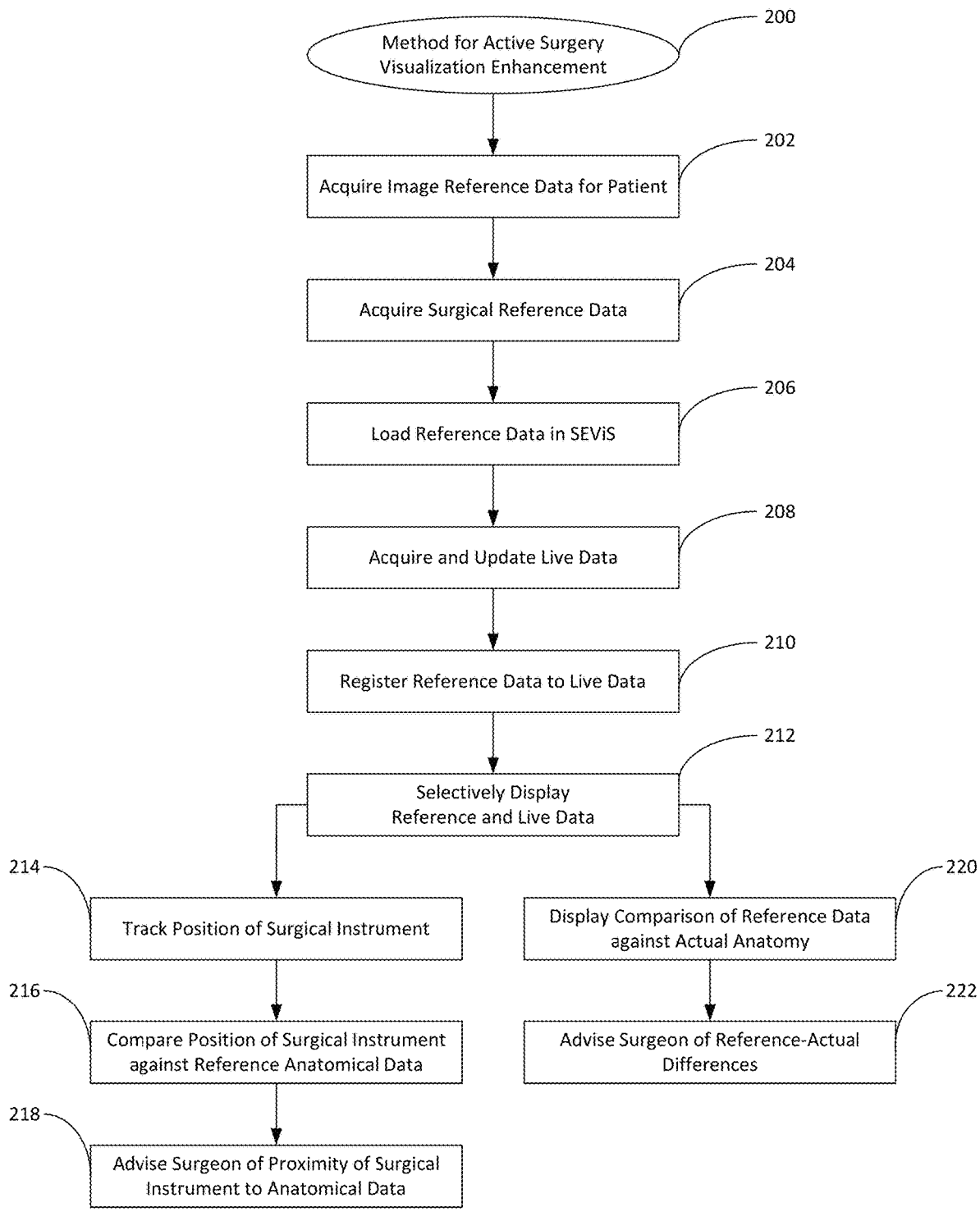
FIG. 7 is a process flowchart showing an embodiment of a method for active surgery visualization enhancement.

Turning to FIG. 7, shown therein is a novel method for active surgery visualization 200. The method 200 includes a number of different steps and it will be appreciated that the some of the steps may be optional and the order of steps may be changed depending on the requirements of a particular application. It will be further observed that the method 200 may be iterative and may include multiple end points.

The method begins at step 202 with the acquisition of image Reference Data for the patient 520. The image Reference Data for the patient 520 may include, for example, images obtained through radiological studies, endoscopic examinations and external photography. At step 204, surgical or procedural Reference Data is acquired. The surgical Reference Data may include information regarding the planned procedure, preferences of the surgeon 514, information about the instruments 508, prosthetics and other medical information. At step 206, the image Reference Data and the surgical Reference Data is loaded into the SEViS 100. It will be appreciated that steps 202, 204 and 206 may take place before the surgical procedure and may be updated during the surgical procedure.

Step 208 takes place in the presence of the patient 520, preferably in the operating suite 500. At step 208, the sensor modules 106 provide the SEViS 100 with Live Data from the operating suite 500. The Live Data may include, as non-limiting examples, live three-dimensional images of the patient 520, audio messages, ambient temperature readings, vital sign information for the patient 520 (temperature, pulse rate, oxygen saturation, blood pressure, etc.) and information about anesthesia and other medications provided to the patient 520. At step 210, the SEViS 100 processes the Live Data and registers the image Live Date with the image Reference Data. At step 212, the SEViS 100 displays selected Live Data and Reference Data.

In exemplary, non-limiting, embodiments, the headset 102 is an augmented reality headset and the surgeon selects which Live and Reference Data should be displayed from a menu presented through the headset 102. The selected Live and Reference Data can then be virtually displayed onto the patient 520 in real time. This permits the surgeon 514 to visualize, for example, Reference Data representing internal organs while looking at the exterior of the patient 520. In some embodiments, the surgeon 514 navigates the menus presented by the SEViS 100 by voice commands, hand gestures, head movements or eye movements.

As an example, the SEViS 100 can be configured to automatically display different information to the surgeon 514 depending on where the surgeon 514 is looking. While the surgeon 514 and headset 102 are oriented toward the patient 520, the headset 102 can be configured to project a first selection of Live and Reference Data for the patient 520 onto the patient 520, with the projected Live and Reference Data automatically registered with the body of the patient 520. In the even the surgeon 514 looks away from the patient 520 in a first direction, the SEViS 100 can be configured to display a second selection of Live and Reference Data, which may be Live and Reference Data that is not configured for a matched overlay with the body of the patient 520. If the surgeon 514 looks away from the patient in a second direction, the SEViS 100 can be configured to display a third selection of Live and Reference Data.

Once the Reference Data and the Live Data have been processed and registered through the SEViS 100, the surgeon 514 can use the SEViS 100 for a variety of novel applications. For example, at step 214, the surgeon 514 can use the SEViS 100 to track the position of a surgical instrument 508 during the course of the surgical procedure. The surgical instrument 508 can be tracked, for example, by the sensors 106 positioned on the surgical instrument 508, through sensor modules 106 mounted in the operating suite 500, or with sensors modules 106 positioned on or inside the patient 520. At step 216, the SEViS 100 compares the position of the surgical instrument 508 as Live Data against the location of specific anatomical elements on or within the patient 520 that have been loaded as Reference Data into the SEViS 100, and thereby determines the proximity of the surgical instrument 508 to the specific anatomical elements on or within the patient 520 during a surgical procedure. For example, the SEViS 100 can compare the position of a scalpel to a critical vascular structure or organ within the operating field to determine the proximity of the scalpel to the vascular structure or organ.

At step 218, the SEViS 100 issues an alert to the surgeon 514 if (when) the instrument 508 gets too close to the designated anatomical features within the patient 520, i.e., when the distance between the surgical instrument 508 and the designated anatomical feature is less than a predetermined number, which may be, for example, in a range from 0.5 millimeter (mm) to 10 mm. The alert may be an audio signal or alarm, a visual signal or alarm displayed through the headset 102 or through a haptic or tactile signal, cue, or response. Thus, the SEViS 100 provides an active warning system to the surgeon 514 in the event a surgical instrument 508 is too close or is in a dangerous proximity to a critical anatomical feature within the patient 520. The alert may include an identifier which identifies or describes the particular anatomical feature. This functionality is particularly useful in procedures in which incisions are made near critical organs or vascular structures that are obscured by intermediate layers of tissue or bone. In certain embodiments, when the surgical instrument 508 reaches a predetermined critical proximity to a particular anatomical feature, the SEViS 100 may automatically stop the movement of the surgical instrument 508 or disable the surgical instrument 508 independently of an action by the surgeon 514.

The SEViS 100 can also be configured to provide an anesthesiologist or other surgical assistant 518 with a warning or indication in the event the surgical instrument 508 encroaches on the predetermined boundary around a particular anatomical feature. As a non-limiting example, if the SEViS 100 detects that the surgical instrument 508 is applying traction to extraocular muscles, it can predict the effect of the oculocardiac reflex (also known as the Aschner phenomenon) and alert the anesthesiologist to a potential for slowing pulse. Similarly, the sensor modules 106 of the SEViS 100 can visually detect and estimate excessive blood loss and inform the surgeon 514 or surgical assistant 518. In some embodiments, the SEViS 100 is also configured to provide a recommendation to the anesthesiologist for a volume of replacement fluids.

In another aspect, the method 200 can be used to assist the surgeon 514 with a procedure that involves precisely matching anatomical features. Such procedures include, for example, plastic surgery in which the surgeon 514 is attempting to change a feature of the patient 520 to match a desired outcome. Other examples include joint replacement or joint repair surgeries in which the surgeon 514 is attempting to match the position or length of a prosthetic so that the augmented anatomy of the patient 520 matches existing or desired anatomy. This functionality begins at step 220 by comparing the Reference Data against the anatomical Live Data from the patient 520.

For example, the SEViS 100 can display through the augmented reality headset 102 a virtualized representation of the proper position of an artificial acetabular cup within the hip socket of the patient 520. The surgeon 514 can then manipulate the acetabular cup within the patient 520 so that it matches the position and orientation of the virtualized prosthetic component displayed through the headset 102. At step 222, the SEViS 100 can advise the surgeon 514 of any misalignments or errors in positioning between the ideal case displayed through the headset 102 and the actual position of the prosthetic in or on the patient 520. Errors in positioning or alignment can be displayed in different colors to quickly and clearly instruct the surgeon 514 how to resolve the positional or alignment errors. When the prosthetic is aligned with the Reference Data for the correct position of the prosthetic, a correct alignment indicator can be displayed to the surgeon 514, for example by changing the color of the virtual display for the prosthetic (e.g., from red to green).

Figure 8:
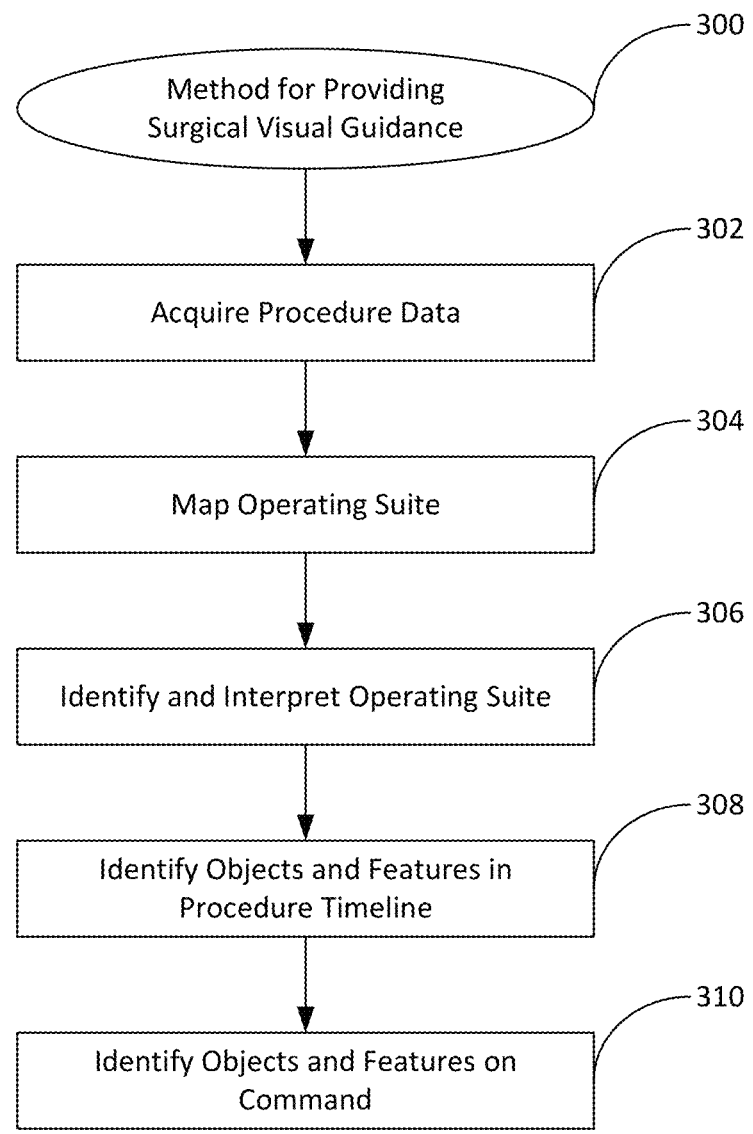
FIG. 8 is a process flowchart showing an embodiment of a method for using a surgical visual guidance system.

Turning to FIG. 8, shown therein is a method 300 for providing surgical visual guidance with the SEViS 100. The method 300 begins with the SEViS 100 acquiring data for the planned procedure. The procedure Reference Data includes information about the procedure, including steps in the procedure, background medical information and preferences for the surgeon 514. At step 304, the sensor modules 106 of the SEViS 100 create a three-dimensional map of the operating suite 500. Using machine learning and pattern recognition functions, the SEViS 100 interprets and identifies objects and people in the operating suite 500 at step 306. The instruments 508 can, for example, be visually identified and their positions recorded within the SEViS 100. Once the instruments 508 and other objects within the operating suite 500 have been identified, the SEViS 100 can integrate these objects into the timeline of the procedure at step 308. Using the sensor modules 106, the SEViS 100 can then track the course of the procedure in real time and provide the surgeon 514, student 516 and surgical assistant 518 with prompts or information about the current and successive steps in the procedure through the headsets 102 at step 310. For example, the SEViS 100 can determine that a cauterization tool is needed for the next step in the procedure and can highlight the appropriate instrument 508 or part of through the headset 102. The same identification system can be used to highlight the portion of the patient 520 that is involved in the next step of the operation.

In yet another aspect, the sensor modules 106 of the SEViS 100 are configured to track the utilization of surgical supplies (e.g., gauze, sponges, compresses, bandages, sutures, etc.), medicines, and surgical instruments 508 in real time. Tracking the utilization of these products in the operating suite 500 can help the surgical facility determine which supplies are consumed during an operation and which are unnecessary. The SEViS 100 can be configured to alert the surgeon 514 or surgical assistant 518 that supplies or other foreign objects are unintentionally left inside the patient 520 during the procedure to minimize the unintended retention of foreign objects (URFO) and retained surgical items (RSIs). The SEViS 100 can also be configured to provide inputs to the surgical facility's billing and practice management systems to optimize the provision of supplies for future operations and the recoupment of costs associated with the consumption of those supplies in the operating suite 500.

In some embodiments, the SEViS 100 is provided with machine learning functionality that is trained to develop a symbolic representation of a standard surgical operation or sequence, or to observe the preferences and actions of a particular surgeon 514. These preferences and actions can be identified, categorized and stored as procedure Reference Data for future use by the surgeon 514, his students 516 or other surgeons in future operations. In this way, the SEViS 100 provides a valuable training tool that automatically determines Reference Data as it observes operations in the operating suite 500. The SEViS 100 can, for example, determine the order of operations that a particular surgeon 514 carries out in a specific surgery and the use that information as surgical Reference Data to guide a new surgeon on best practices for that surgery.

In yet another embodiment, an independent light emitting targeting module 114 (shown in FIG. 1) can be used to automatically emit a visible light on the instrument 508 that is needed by the surgeon 514 for the next step in the operation. The light emitting targeting module 114 can also provide a visible indication on the patient 520 that represents the desired location of an upcoming incision or other surgical action. In exemplary embodiments, the light emitting targeting module 114 includes a laser light system that can be trained on a desired target within the operating suite 500. In some embodiments, the laser light system is mounted on the ceiling or wall of the operating suite 500 and it includes a small laser supported by a motorized mount that rotates and articulates to permits the light emitting targeting module 114 to cast a light beam onto selected targets within the operating suite 500.

In another embodiment, the surgeon 514 or other participant in the operating suite 500 can issue a voice command to the surgical enhanced visualization system 100 for the identification of a specific instrument 508, anatomy of the patient 520 or other object in the operating suite 500. Based on that command, the SEViS 100 will identify the desired object through a virtual highlight in the headset 102 or by emitting a laser light indication on the desired object with the light emitting targeting module 114.

Although the SEViS 100 is shown deployed in a conventional modern operating suite 500, it will be appreciated that the SEViS 100 can also find utility in other environments, including, for example, classrooms, research laboratories, athletic training facilities, kitchens, and manufacturing and assembly facilities. The SEViS 100 can be easily adapted for training and guidance exercises for complicated multistep activities, such as product assembly, vehicle operation and equipment training.

Thus, in one aspect, embodiments of the present invention include a method for enhancing a surgical operation carried out on a patient by a surgeon in an operating suite using a surgical enhanced visualization system. The surgical enhanced visualization system includes one or more sensor modules configured to gather live data from the operating suite, a headset worn by the surgeon, and a computer connected to the headset and the one or more sensor modules. The method includes the steps of acquiring patient reference data, loading the patient reference data and features into the computer, and acquiring live data from the operating suite during the surgical operation, where the live data includes a live three dimensional model of the patient. The method continues with the steps of registering the patient reference data and live data and displaying in real time an overlay of selected registered patient reference data onto the patient through the headset worn by the surgeon.

In another aspect, embodiments of the present invention include a surgical enhanced visualization system for use in assisting a surgeon performing a surgical procedure with a surgical instrument on a patient in an operating suite. The surgical enhanced visualization system includes a computer adapted to store reference data, a sensor module inside the surgical suite, where the sensor module is configured to record live data during the surgical procedure and to transmit the live data to the computer, and an augmented reality headset in communication with the computer and configured to be worn by a surgeon in the operating suite. The augmented reality headset is configured to display both live data and reference data to the surgeon during the surgical procedure.

In yet another aspect, embodiments of the present invention include a method for providing surgical visual guidance during a surgical operation carried out on a patient by a surgeon in an operating suite using a surgical enhanced visualization system that includes one or more sensor modules configured to gather live data from the operating suite, a light emitting targeting module and a computer. The method includes the steps of acquiring surgical procedure data about the surgical operation, loading the surgical procedure data into the computer, and acquiring live data from the operating suite during the surgical operation, where the live data includes the position of instruments within the operating suite. The method continues with the steps of registering the surgical procedure data and live data, and targeting an instrument within the surgical suite in response to a command based on the surgical procedure data.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element. It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the present disclosure is not limited to those diagrams or to the corresponding descriptions. For example, flow need not move through each illustrated box or state, or in exactly the same order as illustrated and described.

Methods of the present disclosure may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be at least ±20%, or at least ±10%, or at least ±5% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded. The range 0.5 mm to 10 mm is to be understood to include all integers within the range and decimal fractions within the range (e.g., 1, 2, 3, 4, 5, 6, 7, 8, 9, and 0.6, 0.7, 0.8, 0.9, 1.1, 1.2, 1.3, 1.4, 1.5, 1.6, 1.7, 1.8, 1.9, and 0.51, 0.52, 0.53, 0.54, 0.55, 0.56, 0.57, 0.58, 0.59, and so on).

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Still further, additional aspects of the various embodiments of the instant disclosure may be found in one or more appendices attached hereto and/or filed herewith, the disclosures of which are incorporated herein by reference as if fully set out at this point.

Thus, the embodiments of the present disclosure are well adapted to carry out the objects and attain the ends and advantages mentioned above as well as those inherent therein. While the inventive device and system have been described and illustrated herein by reference to particular non-limiting embodiments in relation to the drawings attached thereto, various changes and further modifications, apart from those shown or suggested herein, may be made therein by those of ordinary skill in the art, without departing from the spirit of the inventive concepts.

What is claimed is:

1. A method for training a new surgeon comprising the steps of:
   providing an experienced surgeon with a surgical enhanced visualization system that includes one or more sensor modules, a first headset, and a computer connected to the first headset and the one or more sensor modules;
   carrying out a surgical operation on a first patient in an operating suite while the experienced surgeon is wearing the first headset;
   tracking the position of objects and people in the operating suite during the surgical operation with the one or more sensor modules and the first headset;
   using machine learning to identify objects and people in the operating suite during the surgical operation;
   developing a symbolic representation of the surgical operation based on the identification of objects and people in the operating suite during the surgical operation;
   storing the symbolic representation as reference data for carrying out the surgical operation on a second patient;
   loading the symbolic representation as reference data in the surgical enhanced visualization system;
   providing the new surgeon with the surgical enhanced visualization system;
   acquiring live data from the operating suite for the surgical operation on the second patient, wherein the live data includes a live three dimensional model of the second patient;
   registering the symbolic representation and the live data for the second patient; and
   displaying in real time an overlay of the symbolic representation onto the second patient through the headset worn by the new surgeon to guide the new surgeon during the surgical operation on the second patient.

2. The method of claim 1, further comprising the steps of:
   utilizing the symbolic representation to obtain contextually relevant reference data; and
   displaying the contextually relevant reference data through the headset worn by the new surgeon.

3. The method of claim 1 further comprising the step of:
   displaying a beam of visible light onto a target within the operating suite in furtherance of the surgical operation on the second patient and in response to a command from the computer based on the symbolic representation, wherein the target is selected from the group consisting of one or more of a plurality of surgical instruments and the second patient.

4. The method of claim 1, further comprising the steps of:
   acquiring patient reference data for the second patient; and
   loading the patient reference data for the second patient into the computer.

5. The method of claim 4, further comprising the steps of:
extracting features from the patient reference data;
loading the features into the computer;
registering the features with the live data; and
displaying in real time a virtual overlay of selected features onto the patient through the headset worn by the new surgeon.

6. The method of claim 4, further comprising the steps of:
registering the patient reference data with the symbolic representation and the live data; and
displaying in real time an overlay of selected registered patient reference data onto the second patient through the headset worn by the new surgeon.

7. The method of claim 6, wherein the step of acquiring the patient reference data for the second patient comprises acquiring virtualized model prosthetic data about a physical prosthetic to be implanted within the second patient.

8. The method of claim 7, wherein the step of registering the patient reference data comprises registering the virtualized model prosthetic data with live data about the corresponding target anatomy of the second patient.

9. The method of claim 8, further comprising the step of changing the color of the virtualized model prosthetic data depending on whether the physical prosthetic is properly positioned with respect to the virtualized model prosthetic data displayed through the headset worn by the new surgeon.

10. The method of claim 4, further comprising the step of:
tracking the position of a surgical instrument with the one or more sensor modules;
comparing the position of the surgical instrument against the position of anatomical features extracted from the patient reference data for the second patient; and
alerting the new surgeon if the position of the surgical instrument is too close to the position of the anatomical features extracted from the patient reference data.

11. The method of claim 10, wherein the step of tracking the position of the surgical instrument comprises using a sensor positioned on or inside the second patient to track the position of the surgical instrument.

12. The method of claim 10 further comprising the step of:
displaying a beam of visible light onto a target within the operating suite in furtherance of the surgical operation on the second patient and in response to a command from the computer based on the symbolic representation, wherein the target is selected from one or both of the surgical instrument and the second patient.

13. A method of training for a surgical operation using a surgical enhanced visualization system that includes one or more sensor modules, a first headset, and a computer connected to the first headset and the one or more sensor modules, the method comprising the steps of:
providing a first surgeon with the surgical enhanced visualization system;
carrying out a surgical operation on a first patient in an operating suite while the first surgeon is wearing the first headset;
tracking the position of objects and people in the operating suite during the surgical operation with the one or more sensor modules and the first headset;
using machine learning to identify objects and people in the operating suite during the surgical operation;
developing a symbolic representation of the surgical operation based on the identification of objects and people in the operating suite during the surgical operation;
storing the symbolic representation as reference data for carrying out the surgical operation;
loading the symbolic representation as reference data in the surgical enhanced visualization system;
providing the surgical enhanced visualization system to a second surgeon as a tool for performing the surgical operation on a second patient;
acquiring live data for the surgical operation on the second patient, wherein the live data includes a live three dimensional model of the second patient;
registering the symbolic representation and the live data; and
guiding the second surgeon during the surgical operation through information displayed on a headset worn by the second surgeon.

14. The method of claim 13, wherein the step of guiding the second surgeon during the surgical operation comprising displaying in real time an overlay of the symbolic representation onto the second patient through the headset worn by the second surgeon.

15. The method of claim 13, wherein the step of developing the symbolic representation of the surgical operation comprises identifying the preferences and actions of the first surgeon.

16. The method of claim 13, wherein the step of providing the surgical enhanced visualization system to the second surgeon as a tool for performing the surgical operation comprises deploying the surgical enhanced visualization system within an environment selected from an operating suite, a classroom, a research laboratory, and a training facility.

* * * * *